United States Patent
Mo et al.

[11] Patent Number: 6,012,458
[45] Date of Patent: Jan. 11, 2000

[54] METHOD AND APPARATUS FOR TRACKING SCAN PLANE MOTION IN FREE-HAND THREE-DIMENSIONAL ULTRASOUND SCANNING USING ADAPTIVE SPECKLE CORRELATION

[76] Inventors: Larry Y. L. Mo, 1707 Saratoga Rd., Waukesha, Wis. 53186; William Thomas Hatfield, 1305 Keyes Ave., Schenectady, N.Y. 12309; Steven C. Miller, W226 N2572 Aspenwood La., Waukesha, Wis. 53186

[21] Appl. No.: 09/045,780

[22] Filed: Mar. 20, 1998

[51] Int. Cl.$^7$ ..................................................... A61B 8/00
[52] U.S. Cl. ........................................... 128/916; 600/437
[58] Field of Search .................................. 600/437, 441, 600/442, 443, 447; 128/916; 395/124

[56] References Cited

U.S. PATENT DOCUMENTS

| | | | |
|---|---|---|---|
| 5,226,113 | 7/1993 | Cline et al. | 395/124 |
| 5,331,964 | 7/1994 | Trahey et al. | 600/447 |
| 5,485,842 | 1/1996 | Quistgaard | 128/660.07 |
| 5,538,004 | 7/1996 | Bamber | 128/916 |
| 5,582,173 | 12/1996 | Li | 128/660.07 |
| 5,655,535 | 8/1997 | Friemel et al. | 128/660.07 |
| 5,782,766 | 7/1998 | Weng et al. | 128/916 |
| 5,787,889 | 8/1998 | Edwards et al. | 128/916 |
| 5,817,022 | 10/1998 | Vesely | 128/916 |

FOREIGN PATENT DOCUMENTS

WO 97/00482  1/1997  WIPO .

OTHER PUBLICATIONS

Bohs et al., "A Novel Method for Angle Independent Ultrasonic Imaging of Blood Flow and Tissue Motion," IEEE Trans. Biomed. Engng., vol. 38, No. 3, pp. 280–286 (Mar. 1991).

Chen et al., "Determination of Scan–Plane Motion Using Speckle Decorrelation: Theoretical Considerations and Initial Test," Int. J. Imaging Syst. Technol., vol. 8, pp. 38–44 (1997).

Trahey et al., "Angle Independent Ultrasonic Detection of Blood Flow," IEEE Trans. Biomed. Engng., vol. 34, No. 12, pp. 965–967 (Dec. 1987).

Shehada et al., "Ultrasound Methods for Investigating the Non–Newtonian Characteristics of Whole Blood," IEEE Trans. Ultrasonics, Ferroelec. & Freq. Control, vol. 41, No. 1, pp. 96–104 (Jan. 1994).

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for tracking scan plane motion in free-hand three-dimensional ultrasound scanning using adaptive speckle correlation. The method employs a correlation index which adapts to different display dynamic range and post-processing filters. The method may include the following steps: choosing a kernel within each frame image for correlation calculations; rejecting duplicate image frames; measuring the degree of correlation between successive image frames; rejecting correlation estimates which may be associated with hand jitter and other artifacts; and computing the average frame-to-frame (i.e., interslice) spacing based on the average correlation estimate. This image-based motion tracking technique enables three-dimensional reconstruction with good geometric fidelity, without use of any external position-sensing device.

23 Claims, 4 Drawing Sheets

METHOD AND APPARATUS FOR TRACKING SCAN PLANE MOTION IN FREE-HAND THREE-DIMENSIONAL ULTRASOUND SCANNING USING ADAPTIVE SPECKLE CORRELATION

FIELD OF THE INVENTION

This invention generally relates to ultrasound imaging of the human anatomy for the purpose of medical diagnosis. In particular, the invention relates to a method for imaging the human anatomy by detecting the intensity of ultrasonic echoes reflected by a scanned volume in a human body.

BACKGROUND OF THE INVENTION

Conventional ultrasound scanners create two-dimensional B-mode images of tissue in which the brightness of a pixel is based on the intensity of the echo return. The basic signal processing chain in the conventional B mode is depicted in FIG. 1. An ultrasound transducer array 2 is activated to transmit an acoustic burst along a scan line. The return RF signals are detected by the transducer elements and then formed into a receive beam by the beamformer 4. The beamformer output data (I/Q or RF) for each scan line is passed through a B-mode processing chain 6 which includes an equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. The frame averaging may be implemented by a FIR or an IIR filter. In general, the compressed images are in R-θ format (for a sector scan) which is converted by the scan converter 10 into X-Y format for video display. On some systems, frame averaging may be performed on the video X-Y data (indicated by dashed block 12) rather than the acoustic frames before scan conversion, and sometimes duplicate video frames may be inserted between acoustic frames in order to achieve a given video display frame rate (typically 30 Hz). The video frames are passed on to a video processor 14, which basically maps the video data to a display gray map for video display.

System control is centered in a host computer 20, which accepts operator inputs through an operator interface 22 (e.g., a keyboard) and in turn controls the various subsystems. (In FIG. 1, only the image data transfer paths are depicted.) During B-mode imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via track-ball control, and a section of the image loop can be selected for hard disk storage. For an ultrasound scanner with free-hand three-dimensional imaging capability, the selected image sequence stored in cine memory 16 is transferred to the host computer 20 for three-dimensional reconstruction. The result is written back into another portion of the cine memory, from where it is sent to the display system 18 via video processor 14.

Referring to FIG. 2, the scan converter 10 comprises an acoustic line memory 24 and an X-Y memory 26. The B-mode data stored in polar coordinate (R-θ) sector format in acoustic line memory 24 is transformed to appropriately scaled Cartesian coordinate intensity data, which is stored in X-Y memory 26. A multiplicity of successive frames of B-mode data are stored in cine memory 16 on a first-in, first-out basis. The cine memory is like a circular image buffer that runs in the background, continually capturing image data that is displayed in real time to the user. When the user freezes the system, the user has the capability to view image data previously captured in cine memory.

The host computer 20 comprises a central processing unit (CPU) 28 and a random access memory 30. The CPU 28 has read only memory incorporated therein for storing routines used in transforming an acquired volume of intensity data into a multiplicity of three-dimensional projection images taken at different angles. The CPU 28 controls the X-Y memory 26 and the cine memory 16 via the system control bus 32. In particular, the CPU 28 controls the flow of data from the acoustic line memory 24 or from the X-Y memory 26 of the scan converter 10 to the video processor 14 and to the cine memory 16, and from the cine memory to the video processor 14 and to the CPU 28 itself. Each frame of imaging data, representing one of a multiplicity of scans or slices through the object being examined, is stored sequentially in the acoustic line memory 24, in the X-Y memory 26 and in the video processor 14. IN parallel, image frames from either the acoustic line memory or the X-Y memory are stored in cine memory 16. A stack of frames, representing the scanned object volume, is stored in section 16A of cine memory 16.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional volume, the anatomy becomes much easier to visualize for both the trained and untrained observer.

In order to generate three-dimensional images, the CPU 28 can perform a series of transformations using a ray casting algorithm such as the one disclosed in U.S. Pat. Nos. 5,226,113 or 5,485,842. The ray-casting technique is applied to the data for the source data volume of interest retrieved from section 16A of cine memory 16. The successive transformations may involve a variety of projection techniques such as maximum, minimum, composite, surface or averaged projections made at angular increments, e.g., at 10° intervals, within a range of angles, e.g., +90° to −90°. Each pixel in the projected image includes the transformed data derived by projection onto a given image plane. In addition, at the time when the cine memory was frozen by the operator, the CPU 28 optionally stores the last frame from the X-Y memory 28 at multiple successive addresses in section 16B of cine memory 16. The projected image data for the first projected view angle is written into the first address in cine memory section 16B, so that the projected image data in a region of interest is superimposed on the background frame. This process is repeated for each angular increment until all projected images are stored in cine memory section 16B, each projected image frame consisting of a region of interest containing transformed intensity data and optionally a background perimeter surrounding the region of interest consisting of background intensity data not overwritten by the transformed intensity data. The background image makes it clearer where each displayed projection is being viewed from. The operator can then select any one of the projected images for display. In addition, the sequence of projected images can be replayed on the display monitor to depict the object volume as if it were rotating in front of the viewer.

Various types of multi-row transducer arrays, including so-called "1.25D" and "1.5D" arrays, have been developed to improve upon the limited elevation performance of present single-row ("1") arrays. As used herein, these terms have the following meanings: 1D) elevation aperture is fixed and focus is at a fixed range; 1.25D) elevation aperture is variable, but focusing remains static; and 1.5D) elevation aperture, shading, and focusing are dynamically variable, but symmetric about the centerline of the array.

In free-hand three-dimensional ultrasound scans, a transducer array (1D to 1.5D) is translated in the elevation direction to acquire a substantially parallel set of image planes through the anatomy of interest. These images can be stored in the cine memory and later retrieved by the system computer for three-dimensional reconstruction. If the spacings between image frames are known, then the three-dimensional volume can be reconstructed with the correct aspect ratio between the out-of-plane and scan plane dimensions. If, however, the estimates of the interslice spacing are poor, significant geometric distortion of the three-dimensional object can result.

In the prior art, a variety of motion control and position-sensing methods have been proposed to control or track the elevational motion of the probe respectively. However, these systems are often costly and cumbersome to use in a clinical environment. Therefore, to reconstruct a three-dimensional image with good resolution in the elevation direction, it is highly desirable to be able to estimate the scan plane displacements directly from the degree of speckle decorrelation between successive image frames.

In International Patent WO 97/00482, Fowlkes et al. proposed a scan plane motion tracking method which is based on computing the correlation between image frames. It was stated that their correlation method is an adaptation of the decorrelation techniques used for monitoring blood flow. A review of such prior art indicates that there are two general approaches as follows:

(1) Trahey et al., in "Speckle pattern correlation with lateral aperture translation: experimental results and implications for spatial compounding," IEEE Trans. Ultrasonics, Ferroelec. and Freq. Control, Vol. UFFC-33 (1986), pp. 257–264, reported the first study that used a full correlation function of intensities in ultrasound images. This approach uses RF or detected image data prior to compression, which is evident from the fact that the correlation function is normalized by the total echo intensities (i.e., is system gain dependent). Chen et al., in "Determination of scan-plane motion using speckle decorrelation: theoretical considerations and initial test," Int. J. Imaging Syst. Technol., Vol. 8 (1997), pp. 38–44, reported phantom studies using this correlation method for three-dimensional sweep distance estimation.

(2) Bohs et al., in "A novel method for angle independent ultrasonic imaging of blood flow and tissue motion," IEEE Trans. Biomed. Eng., Vol. 38 (1991), pp. 280–286, proposed a simpler correlation method which should work with compressed ultrasound images. This is referred to as the SAD method since it is based on computing the sum of absolute differences between corresponding pixels in two kernels being correlated. This computationally efficient method was found to perform almost as well as the full correlation function of Trahey et al. Shehada et al., in "Ultrasound methods for investigating the non-Newtonian characteristics of whole blood," IEEE Trans. Ultrasonics, Ferroelec. and Freq. Control, Vol. UFFC-41 (1994), pp. 96–104, also reported a flow measurement study based on SAD correlation of ultrasound images. For flow measurement, the SAD method basically consists of finding the displacement vector within the scan plane that minimizes the SAD, so only relative changes in SAD are pertinent. In general, however, for a given kernel size the SAD can vary significantly with dynamic range setting and post-processing filtering.

On ultrasound scanners with three-dimensional free-hand scan capability, the images stored in cine memory typically have already gone through a logarithmic or some other highly nonlinear compression for display (typically an 8-bit amplitude display). These images may have also gone through some post-processing filters such as for smoothing or edge enhancement. The compression and filtering operations are often not reversible, and any attempt to make even an approximate "decompression" may introduce quantization noise in the images. For this reason, the first approach discussed above, which is designed for pre-compressed images, may not be most suitable for sweep speed estimation.

The SAD approach works with compressed images and has the advantage of computational speed. However, for three-dimensional reconstruction we need to quantify the actual decorrelation from frame to frame in order to estimate the sweep distance. Using SAD alone would require calibration for all possible combinations of display dynamic range (which may be depth dependent), filters, kernel size and kernel depth position.

Thus, there is a need for a new correlation index that adapts to different dynamic range settings and post-processing filters.

SUMMARY OF THE INVENTION

The present invention is a method and an apparatus for tracking scan plane motion in free-hand three-dimensional ultrasound scanning using adaptive speckle correlation. The method employs a correlation index which adapts to different display dynamic range and post-processing filters. The apparatus in accordance with one preferred embodiment comprises: means for choosing a kernel within each image frame for correlation calculations; means for rejecting duplicate image frames; means for measuring the degree of correlation between successive image frames; means for rejecting correlation estimates which may be associated with hand jitter and other artifacts; and means for computing the average frame-to-frame (i.e., interslice) spacing based on the average correlation estimate. These means are incorporated into a host computer which interfaces with the cine memory. A major benefit of this image-based motion tracking technique is that it enables three-dimensional reconstruction with good geometric fidelity, without use of any external position-sensing device.

DETAILED DESCRIPTION OF THE PREFERRED EMBODIMENTS

Figure 1:
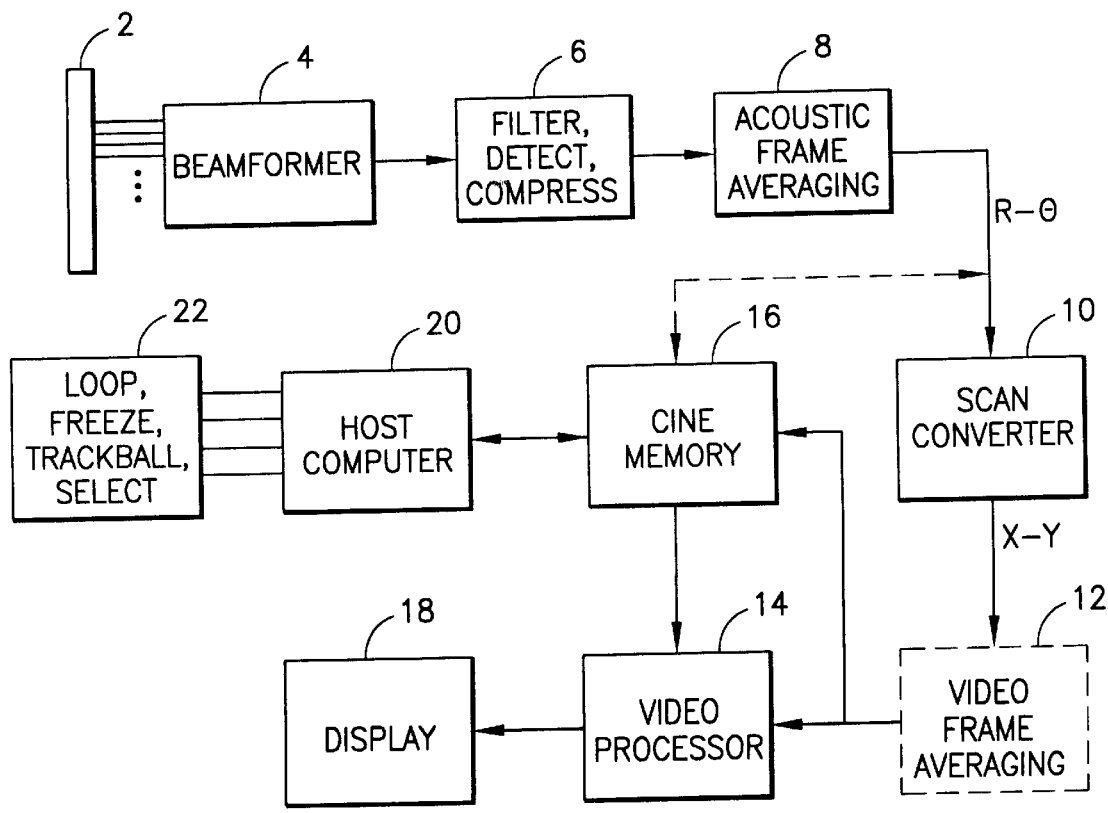
FIG. 1 is a block diagram showing the major functional subsystems within a real-time ultrasound imaging system.
Figure 3:
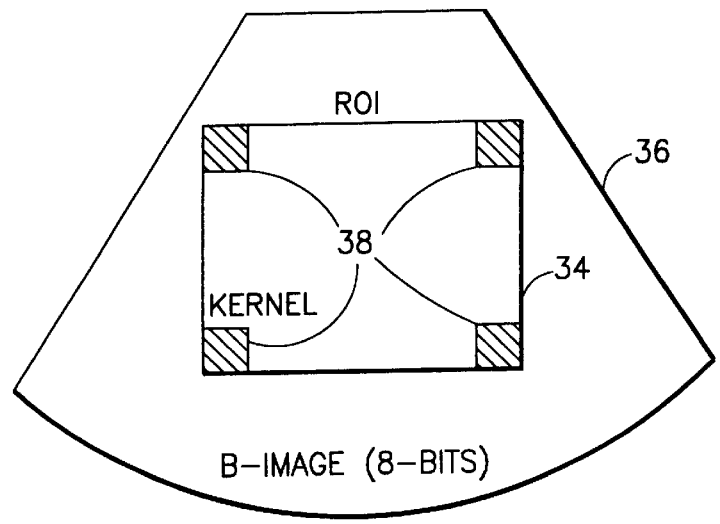
FIG. 3 is a schematic showing a typical region-of-interest box within one image frame and further showing a selected kernel within the region of interest.

FIG. 3 shows a typical region-of-interest (ROI) box 34 within one image frame 36 (a sector scan in this example) as selected by the user. Assume that N frames generated by a free-hand scan are stored in cine memory. The process of estimating the average frame-to-frame spacing d for three-dimensional reconstruction (which is performed by the host computer based on the data retrieved from cine memory) is described in FIG. 4. First, a kernel 38 (M×M pixels in this example, but in general the kernel does not have to be square) within the ROI 34 that shows a relatively pure speckle pattern (no macroscopic structures) must be identified (step 40) since the correlation method in the present invention is based on the statistics of pure speckle arising from a diffuse scattering medium. The kernel 38 can be selected manually (e.g., by means of a trackball) based on visual judgment of one or more image frames. Alternatively, some automated method can be used to search for a kernel whose pixel amplitude histogram is consistent with the theoretical speckle distribution. For example, such tests can be based on a measure of the histogram width relative to normal dynamic range settings. Kernels whose mean pixel values are too low (no signal) or whose variances are too large (not homogeneous) should be rejected. As shown in FIG. 3, a good initial kernel 38 to test is one at any of the four corners of the ROI 34—assuming the user tends to position the structures of interest in the center of the ROI.

Figure 4:
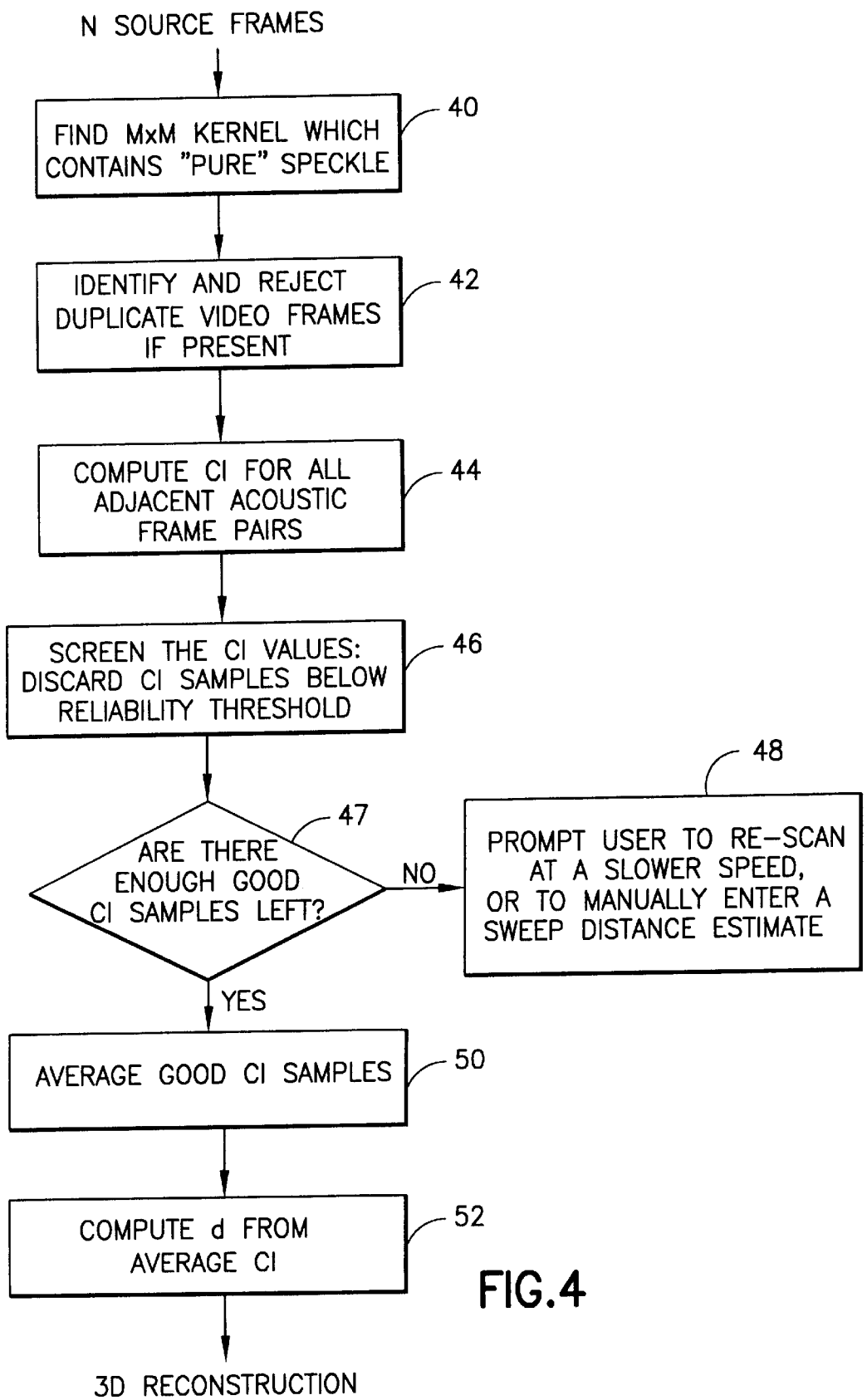
FIG. 4 is a flowchart showing the steps of the method in accordance with the preferred embodiment by which the average frame-to-frame spacing d is estimated for use in three-dimensional reconstruction.

Before proceeding to compute the correlation between kernels in successive image frames, any duplicate image frames present in the N source frames are identified and rejected (step 42 in FIG. 4). Duplicate frames are sometimes inserted in between acoustic image frames in order to match the video monitor display rate (typically 30 Hz). If the duplicate frame pairs are exactly identical, they can be easily detected based on the criterion that the SAD be substantially equal to zero. If the duplicate frames are not exactly identical, due, for example, to frame averaging effects, then some thresholding method may be used to detect the nearly identical frames. For example, if more than some percentage (say 25%) of the pixels in the kernel of a new image frame differ from those in the previous frame by more than some value, then the new image frame passes as a new acoustic frame; otherwise it is considered as a duplicate image frame which is to be rejected. Alternatively, for improved reliability in screening out duplicate frames, it may be necessary to consider the ensemble statistics of SAD values for all (N−1) source frame pairs, and to discard the frames having SAD values that lie outside normal statistical deviations.

Having screened out possible duplicate frames, the next step (step 44 in FIG. 4) is to compute a correlation index (CI) for all adjacent frame pairs in the remaining set of acoustic frames. In the invention, a correlation index is used which can be considered as a normalized SAD that can adapt to different kernel sizes, display dynamic ranges and post-processing filters. This index is advantageous because it is much more computationally efficient than the full correlation function disclosed by Chen et al., which requires image decompression and may use up to 10 frames for each correlation function estimate. The correlation index of the invention ranges from 100% for identical kernels to zero for completely independent speckle patterns. In principle, the correlation index may also become negative if the two kernels pick up different structures.

In general, there is no guarantee that the kernel chosen based on one frame will also contain a homogeneous speckle pattern in other frames. Hence, a screening test (step 46 in FIG. 4) of the correlation index estimates is in order. For example, we may choose to discard all correlation index samples below a certain reliability threshold (e.g., 20%) that are indicative of axial and/or lateral scan-plane jitter, a skid in the elevation motion, or frame averaging (which can make uncorrelated frames look weakly correlated). It may also be useful to count the remaining good correlation index values (step 47 in FIG. 4) to see if they constitute a significant fraction of the N frames (e.g., "at least 10% of the correlation index values must be good"). If too few frames are reliable (CI>20%), then the user should be prompted (step 48) to either re-scan at a slower and more steady speed, or to manually enter an estimate of the total sweep distance.

Figure 2:
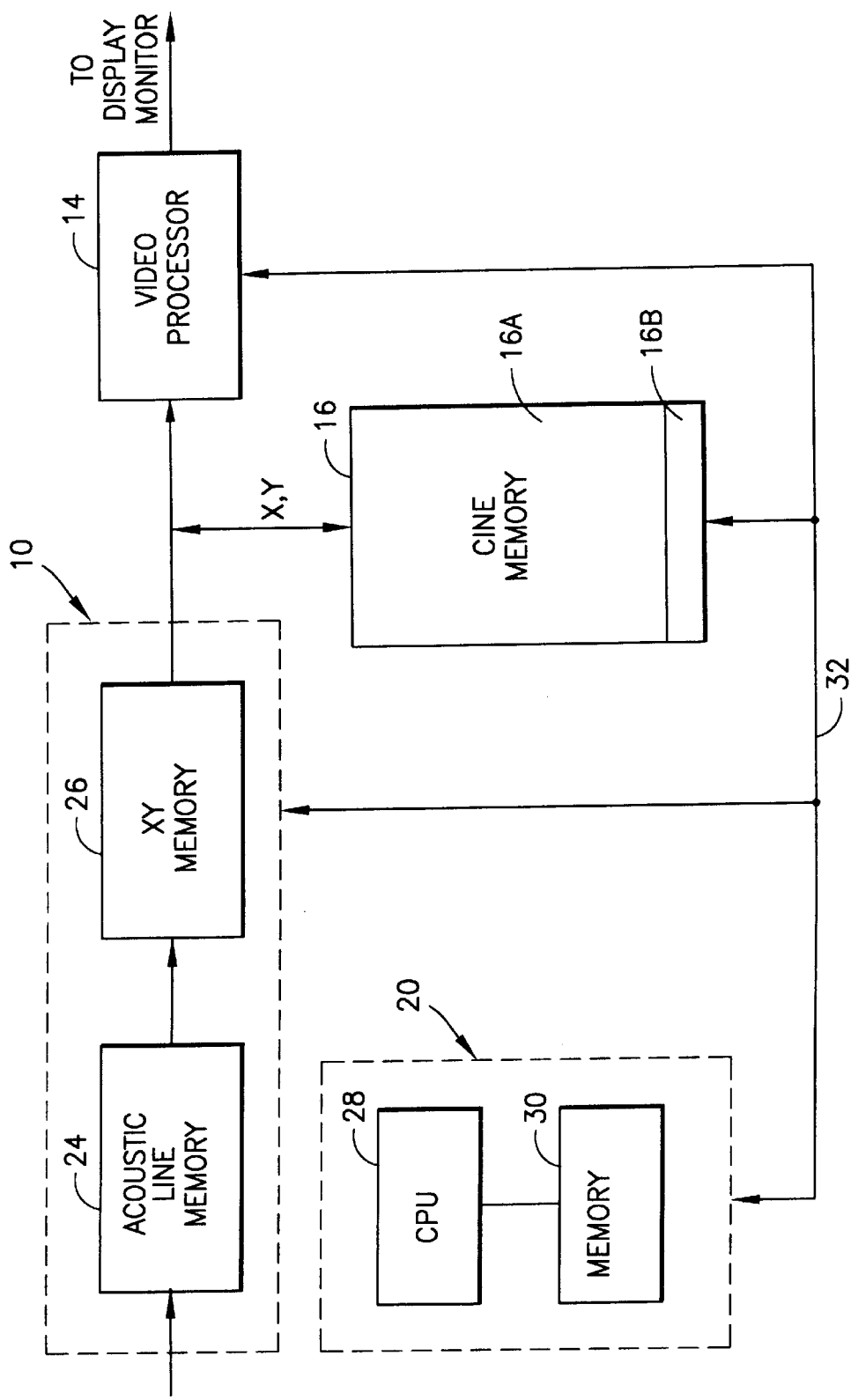
FIG. 2 is a block diagram showing means for reconstructing frames comprising successive volumetric projections of pixel intensity data.

If there are enough good correlation index samples, their average should be taken (step 50 in FIG. 4) to reduce statistical variability. The result can be used to compute the corresponding average interslice spacing d (step 52), based on a pre-calibrated CI versus d model (stored in memory in the CPU 28 shown in FIG. 2) for each probe type and kernel depth. If there are enough good correlation index samples, the corresponding average d should be quite reliable for three-dimensional reconstruction.

At the heart of the invention is an adaptive method for normalizing the SAD of two image kernels such that the resultant correlation index is independent of display dynamic range, post-processing filter and kernel size to within reasonable limits. The key idea is to determine from theoretical speckle statistics what the average SAD per pixel would approach if the image kernels were so far apart that they become statistically independent (if there is no frame averaging).

It is well known that the detected speckle amplitude for a diffuse homogeneous scattering medium is described by a Rayleigh distribution. Suppose the image compression prior to display can be modeled by a simple logarithmic function as follows:

$$y = 10 \log[x+1] \tag{1}$$

Figure 5A:
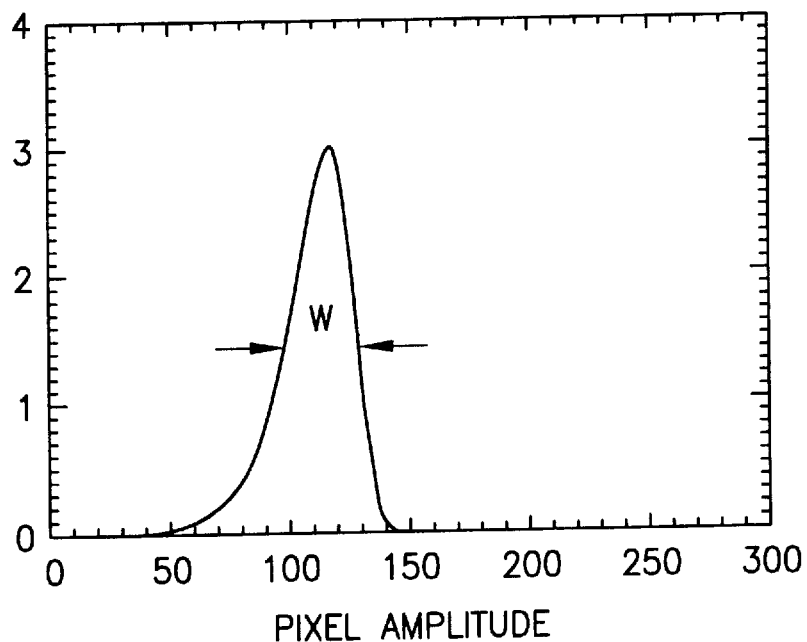
FIG. 5A is a graph showing the probability density distribution $f_y(y)$ of the log-compressed noise spectral power y for m=100, where m=E[x] is the expected value of x.

Standard statistical operations indicate that if x is Rayleigh distributed, then the probability density function (pdf) of y is $$f_y(y) = \frac{a}{m}\exp(ay)\exp\left(-\frac{1}{m}[\exp(ay) - 1]\right) \tag{2}$$

where $a=(0.1)\ln(10)$ is a constant, and $m=E[x]$ is the expected value of x which is dependent on system gain. For an 8-bit linear gray map, y is mapped to [0, 255] for display and a sample histogram for m=100 is plotted in FIG. 5A.

Figure 5B:
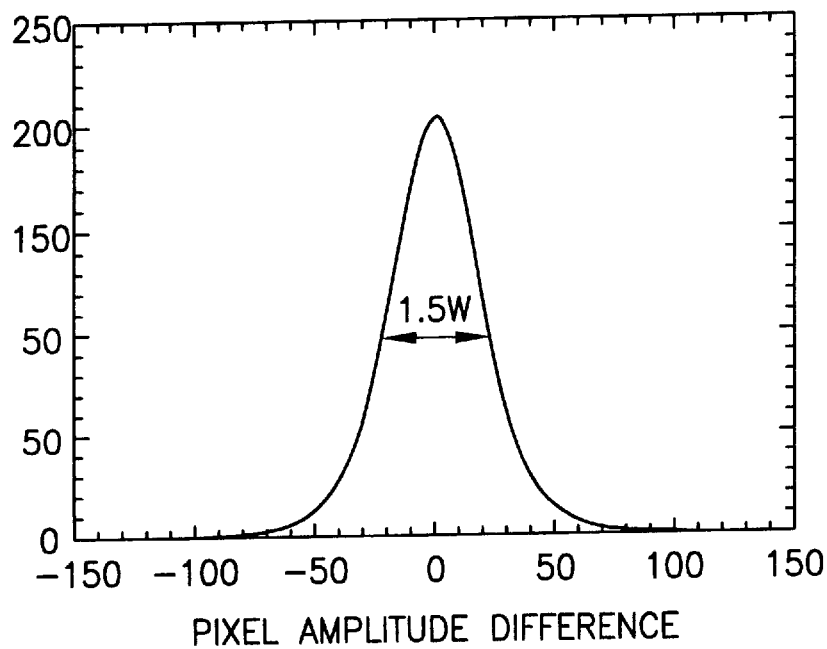
FIG. 5B is a graph showing the probability density distribution $f_y(SAD=|y_1-y_2|)$, where $y_1$ and $y_2$ are independent identically distributed random variables that represent the amplitude of corresponding pixels in two kernels being correlated.

Suppose $y_1$ and $y_2$ are independent identically distributed random variables that represent the amplitude of corresponding pixels in the two kernels being correlated. We need to determine the pdf of $SAD=|y_1-y_2|$. First, the pdf of $(-y_2)$ is simply the mirror image of that of $y_2$, which is assumed to be the same as that of $y_1$. The pdf of $y_1+(-y_2)$ is given by the convolution of their respective pdfs, which is shown in FIG. 5B. Since the pdf of the sum is a symmetric function about zero, the pdf of its absolute value (SAD) is simply the positive half of the distribution (times two).

Note that the half-maximum width w of the pdf of $(y_1-y_2)$ (FIG. 5B) is about 1.5 times that of an individual y (FIG.

5A). In practice, the compression function may be different from Eq. (1), but one can always follow the same approach to derive the pdf of SAD. If the compression function does not deviate greatly from Eq. (1) and the post-processing spatial filtering effects are mild, the width of the SAD histogram can be approximated by a constant $\gamma$ times that of each image kernel, where $\gamma \cong 1.5$. If the spatial filters are very strong, then the value of $\gamma$ may have to be adjusted accordingly. To those skilled in the art it is clear that the width of the pixel amplitude distribution over an (M×M) pixel kernel in the k-th image frame can also be defined by its rms pixel value, or in accordance with the preferred embodiment, by simply the average absolute deviation as follows:

$$s_k = \frac{1}{M^2} \sum \left| y_k(i) - \text{mean}_k \right| \quad (3)$$

in which $y_k(i)$ is amplitude of the i-th pixel, and $\text{mean}_k$ is the mean amplitude over all $M^2$ pixels. In general, Sk is a function of dynamic range setting and post-processing spatial filters.

Suppose the $SAD_k$ image has been computed for two corresponding kernels in the k-th and (k+1)-th frames as follows:

$$SAD_k = \sum_i |y_{k+1}(i) - y_k(i)| \quad (4)$$

As the frame separation increases, the average absolute difference per pixel, i.e., $SAD_k/M^2$, will increase from zero to a limiting value of $(\gamma s_k)$ as the two kernels become statistically independent. Hence, a suitable correlation index can be defined as follows:

$$CI_k = \frac{\gamma s_k - |SAD_k|/M^2}{\gamma s_k} \quad (5)$$

in which $\gamma \cong 1.5$ for a log-compressed speckle image.

Experiments performed using different types of imaging arrays indicated that the correlation index can be described very well by an exponential decay function in interslice spacing d as follows:

$$CI = \exp(-d/D_z) \quad (6)$$

where $D_z$ is the decorrelation length which is a characteristic of the elevational beam profile of the probe. Since the elevational beam profile varies with depth due to diffraction and tissue attenuation effects, $D_z$ is generally a function of depth z for a given transmit frequency. Since the beam profile is generally less coherent and complex in the near field, $D_z$ is expected to be smaller in the near field than in the mid and far fields.

Given a correlation index estimate, the corresponding interslice spacing can be computed as follows:

$$d = -D_z \ln(CI) \quad (7)$$

The fact that CI decays exponentially with d may prove to be an advantage for three-dimensional scanning: CI is very sensitive to small displacements or slow motion. As d increases beyond the elevational slice thickness, CI tapers off slowly towards zero. From Eq. (7), for CI<20%, a small variation in CI can translate into a large change in d. Hence, a reasonable reliability threshold (step 46 in FIG. 4) for rejecting bad correlation index samples is CI=20%, for example; that is, any value below the threshold may be caused by hand jitter or skidding of the probe. Equation (7) can be used to compute the average interslice spacing for the N frames based on the average value of all correlation index values greater than the reliability threshold.

Rather than use a processor to compute the average interslice spacing d during scanning, the relationship between d and CI can be specified by other means, such as a look-up table. However, the exponential model of Eq. (6) offers the convenience that at each depth, the relationship is completely specified by a decorrelation length. For a given probe, the decorrelation lengths for different depths or z-intervals can be calibrated by performing a controlled experiment wherein a motor-driven probe-holder is used to translate the probe at constant speed over a homogeneous scattering phantom.

In the derivation of CI, no frame averaging was assumed. In practice, frame averaging tends to produce additional correlation between adjacent acoustic frames no matter how far apart they are spaced. This means that frame averaging will cause the correlation index to decay more slowly with increasing d (larger effective $D_z$) and towards some non-zero baseline level depending on the degree of frame averaging. This has been confirmed in experimental studies which showed that the exponential decay model of Eq. (6) still holds as long as a larger effective $D_z$ is used and the reliability threshold for the correlation index is chosen above the non-zero baseline correlation associated with frame averaging effects.

The foregoing preferred embodiments have been disclosed for the purpose of illustration. Variations and modifications of the basic concept of the invention will be readily apparent to persons skilled in the art. In particular, it will be appreciated that the invention can be used to compute a spacing between adjacent scan planes which is not an average value. All such variations and modifications are intended to be encompassed by the claims set forth hereinafter.

It is claimed:

1. A system for three-dimensional imaging of an object volume, comprising:

an ultrasound transducer array for transmitting ultrasound beams and detecting ultrasound echoes reflected from said object volume at a multiplicity of sample volumes in a scan plane;

means coupled to said ultrasound transducer array for acquiring imaging data derived from ultrasound echoes reflected from each one of a multiplicity of scan planes through said object volume;

means for storing data for each of a multiplicity of image frames corresponding to said multiplicity of scan planes;

means for determining a degree of correlation between the data of respective kernels of respective pairs of successive image frames, said respective degree of correlation being a function of a normalized sum of the absolute differences between corresponding data of said respective kernels;

means for computing, as a function of said degree of correlation, a spacing between successive ones of said multiplicity of scan planes;

a display monitor; and means for displaying a projected image on said display monitor which is a function of said spacing.

2. The system as defined in claim 1, wherein said spacing is an average value.

3. The system as defined in claim 1, wherein said means for determining a degree of correlation comprise means for screening out substantially duplicate successive image frames.

4. The system as defined in claim 3, wherein said means for screening out substantially duplicate successive image frames comprise means for comparing said sum of absolute differences to a threshold.

5. The system as defined in claim 1, wherein said means for determining a degree of correlation comprise means for estimating a respective correlation index for each pair of successive image frames and means for averaging said correlation index estimates.

6. The system as defined in claim 5, wherein said spacing has a value d which is determined in accordance with the following equation:

$$d = -D_z \ln(CI)$$

where $D_z$ is a decorrelation length which is a characteristic of an elevational beam profile of said ultrasound transducer array and CI is an average of said correlation index estimates.

7. The system as defined in claim 6, wherein said means for computing a spacing comprises a look-up table storing said value d.

8. The system as defined in claim 6, wherein said means for computing a spacing comprises a processor and means for inputting said decorrelation length $D_z$ into said processor.

9. A system for tracking scan plane motion, comprising:

an ultrasound scanner for transmitting ultrasound beams and detecting ultrasound echoes reflected from a multiplicity of scan planes;

means coupled to said ultrasound scanner for acquiring data for each of a multiplicity of image frames, the data for each of said imaging frames being derived from ultrasound echoes reflected from a respective one of said scan planes;

means for determining a degree of correlation between the data of respective kernels of respective pairs of successive image frames, said respective degree of correlation being a function of a normalized sum of the absolute differences between corresponding data of said respective kernels; and means for computing, as a function of said degree of correlation, a spacing between successive ones of said multiplicity of scan planes.

10. The system as defined in claim 9, wherein said spacing is an average value.

11. The system as defined in claim 9, wherein said means for determining a degree of correlation comprise means for screening out substantially duplicate successive image frames.

12. The system as defined in claim 11, wherein said means for screening out substantially duplicate successive image frames comprise means for comparing said sum of absolute differences to a threshold.

13. The system as defined in claim 9, wherein said means for determining a degree of correlation comprise means for estimating a respective correlation index for each pair of successive image frames and means for averaging said correlation index estimates.

14. The system as defined in claim 13, wherein said spacing has a value d which is determined in accordance with the following equation:

$$d = -D_z \ln(CI)$$

where $D_z$ is a decorrelation length which is a characteristic of an elevational beam profile of said ultrasound transducer array and CI is an average of said correlation index estimates.

15. The system as defined in claim 14, wherein said means for computing a spacing comprises a look-up table storing said value d.

16. The system as defined in claim 14, wherein said means for computing a spacing comprises a processor and means for inputting said decorrelation length $D_z$ into said processor.

17. A method for tracking scan plane motion, comprising:

manually scanning an ultrasound scanner across an object;

operating the ultrasound scanner to transmit ultrasound beams and detect ultrasound echoes reflected from a multiplicity of scan planes;

acquiring data for each of a multiplicity of image frames, the data for each of said imaging frames being derived from ultrasound echoes reflected from a respective one of said scan planes;

determining a degree of correlation between the data of respective kernels of respective pairs of successive image frames, said respective degree of correlation being a function of a normalized sum of the absolute differences between corresponding data of said respective kernels; and computing, as a function of said degree of correlation, a spacing between successive ones of said multiplicity of scan planes.

18. The method as defined in claim 17, wherein said spacing is an average value.

19. The method as defined in claim 17, wherein said step of determining a degree of correlation comprises the step of screening out substantially duplicate successive image frames.

20. The method as defined in claim 19, wherein said step of screening out substantially duplicate successive image frames comprise the step of comparing said sum of absolute differences to a threshold.

21. The method as defined in claim 17, wherein said step of determining a degree of correlation comprises the steps of estimating a respective correlation index for each pair of successive image frames and averaging said correlation index estimates.

22. The method as defined in claim 21, wherein said spacing has a value d which is determined in accordance with the following equation:

$$d = -D_z \ln(CI)$$

where $D_z$ is a decorrelation length which is a characteristic of an elevational beam profile of said ultrasound scanner and CI is an average of said correlation index estimates.

23. The method as defined in claim 17, wherein said step of determining a degree of correlation is preceded by the step of identifying a kernel within a region of interest of an image frame that has a speckle pattern consistent with the absence of macroscopic structures.

* * * * *